United States Patent
DeCant, Jr. et al.

(10) Patent No.: US 6,786,884 B1
(45) Date of Patent: Sep. 7, 2004

(54) BOLUS TIP DESIGN FOR A MULTI-LUMEN CATHETER

(75) Inventors: Leonard J. DeCant, Jr., Wexford, PA (US); Vincent J. Belusko, Los Angeles, CA (US); Attilio E. DiFiore, Taylorsville, UT (US)

(73) Assignee: Bard Access Systems, Inc., Salt Lake City, UT (US)

(*) Notice: Subject to any disclaimer, the term of this patent is extended or adjusted under 35 U.S.C. 154(b) by 0 days.

(21) Appl. No.: 09/429,857

(22) Filed: Oct. 29, 1999

(51) Int. Cl.[7] .......................... A61M 3/00; A61M 37/00
(52) U.S. Cl. .......................................... 604/43; 604/6.16
(58) Field of Search ..................... 604/27, 29, 43–45, 604/164.01, 264–266, 523, 533, 537, 538, 284, 6.16

(56) References Cited

U.S. PATENT DOCUMENTS

| | | |
|---|---|---|
| 1,696,018 A | 12/1928 | Schellberg |
| 1,879,249 A | 2/1932 | Honsaker |
| 3,881,254 A | 5/1975 | Epstein |
| 4,134,402 A | 1/1979 | Mahurkar |
| 4,270,542 A | 6/1981 | Plumley |
| 4,311,140 A | 1/1982 | Bridgman |
| 4,381,011 A | 4/1983 | Somers, 3rd |
| 4,388,076 A | 6/1983 | Waters |
| 4,390,017 A | 6/1983 | Harrison et al. |
| 4,410,320 A | 10/1983 | Dykstra et al. |
| D272,651 S | 2/1984 | Mahurkar |
| 4,490,143 A | 12/1984 | Quinn et al. |
| 4,496,347 A | 1/1985 | MacLean et al. |
| 4,516,970 A | 5/1985 | Kaufman et al. |
| 4,552,554 A | 11/1985 | Gould et al. |
| 4,568,329 A | 2/1986 | Mahurkar |
| 4,583,968 A | 4/1986 | Mahurkar |
| 4,594,074 A | 6/1986 | Andersen et al. |
| 4,623,327 A | 11/1986 | Mahurkar |
| 4,626,240 A | * 12/1986 | Edelman et al. ............... 604/43 |

(List continued on next page.)

FOREIGN PATENT DOCUMENTS

| | | |
|---|---|---|
| CA | 1 150 122 | 7/1983 |
| EP | 0 495 263 A1 | 7/1992 |
| FR | 900.765 | 7/1945 |
| GB | 745379 | 2/1956 |
| WO | WO 97/17102 | 5/1997 |
| WO | PCT/US00/29522 | 1/2001 |
| WO | WO 02/062407 A2 | 8/2002 |
| WO | WO 02/092159 A1 | 11/2002 |

*Primary Examiner*—Michael J. Hayes
(74) *Attorney, Agent, or Firm*—Morrison & Foerster LLP

(57) ABSTRACT

An improved bolus tip design for use in a multi-lumen catheter for the simultaneous injection and withdrawal of fluids to and from a patient. The improved bolus tip has a rounded elongate body consisting of an interfacing section and a nose section. A first channel opens to a first bolus cavity, which is formed into the bolus tip, and a second channel either extends through the nose section of the bolus tip, forming an outlet therefrom, or terminates at a second bolus cavity similar to the first bolus cavity. In the latter configuration, the second bolus cavity is located longitudinally between the fist bolus cavity and a tip of the nose section on a side directly opposite the first bolus cavity. The second bolus cavity is in fluid communication with the second channel.

15 Claims, 4 Drawing Sheets

U.S. PATENT DOCUMENTS

| | | |
|---|---|---|
| 4,692,141 A | 9/1987 | Mahurkar |
| 4,770,652 A | 9/1988 | Mahurkar |
| 4,808,155 A | 2/1989 | Mahurkar |
| 4,842,582 A | 6/1989 | Mahurkar |
| 4,895,561 A | 1/1990 | Mahurkar |
| 4,986,807 A | 1/1991 | Farr |
| 4,995,865 A | 2/1991 | Gahara et al. |
| 5,167,623 A | 12/1992 | Cianci et al. |
| 5,171,216 A * | 12/1992 | Dasse et al. .............. 604/43 |
| 5,197,951 A | 3/1993 | Mahurkar |
| 5,221,255 A | 6/1993 | Mahurkar et al. |
| 5,221,256 A | 6/1993 | Mahurkar |
| 5,242,398 A | 9/1993 | Knoll et al. |
| 5,348,536 A | 9/1994 | Young et al. |
| 5,374,245 A | 12/1994 | Mahurkar |
| 5,378,230 A | 1/1995 | Mahurkar |
| 5,395,316 A | 3/1995 | Martin |
| 5,451,206 A | 9/1995 | Young |
| 5,451,216 A | 9/1995 | Quinn |
| 5,451,233 A | 9/1995 | Yock |
| 5,472,417 A | 12/1995 | Martin et al. |
| 5,486,159 A | 1/1996 | Mahurkar |
| 5,571,093 A | 11/1996 | Cruz et al. |
| 5,599,322 A | 2/1997 | Quinn |
| 5,607,462 A | 3/1997 | Imran |
| 5,624,392 A | 4/1997 | Saab |
| 5,665,067 A | 9/1997 | Linder et al. |
| 5,738,649 A | 4/1998 | Macoviak |
| 5,792,094 A | 8/1998 | Stevens et al. |
| 5,797,869 A | 8/1998 | Martin et al. |
| 5,807,318 A | 9/1998 | St. Goar et al. |
| 5,810,787 A | 9/1998 | Quinn |
| 5,810,789 A * | 9/1998 | Powers et al. .............. 604/280 |
| 5,814,016 A | 9/1998 | Valley et al. |
| 5,830,196 A * | 11/1998 | Hicks .................... 604/523 |
| 5,961,486 A | 10/1999 | Twardowski et al. |
| 6,280,423 B1 | 8/2001 | Davey et al. |
| 6,409,700 B1 | 6/2002 | Siegel, Jr. et al. |
| 6,461,321 B1 | 10/2002 | Quinn |
| 6,517,529 B1 | 2/2003 | Quinn |
| 6,540,714 B1 | 4/2003 | Quinn |

* cited by examiner

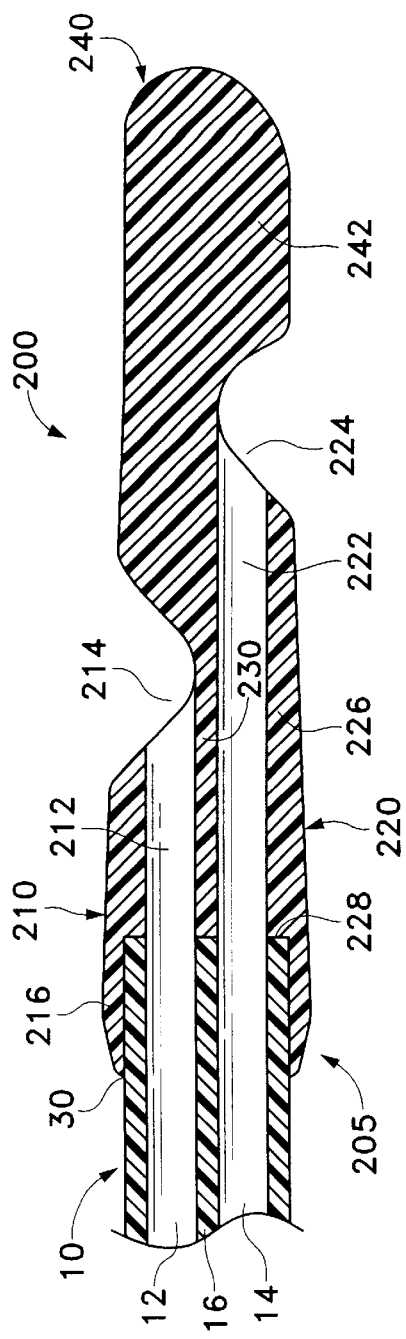
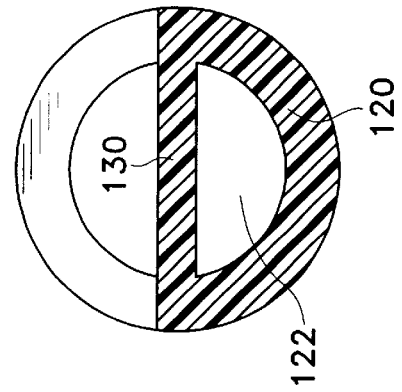
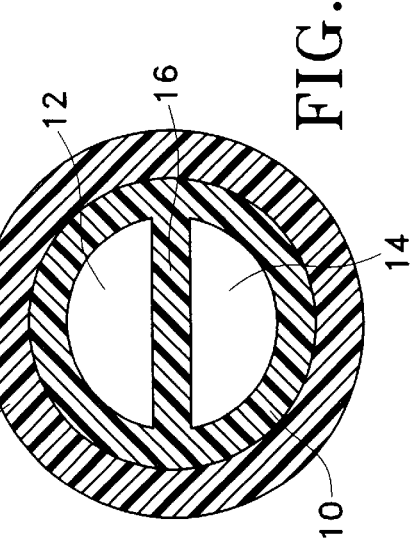
FIG. 3
FIG. 4
FIG. 5

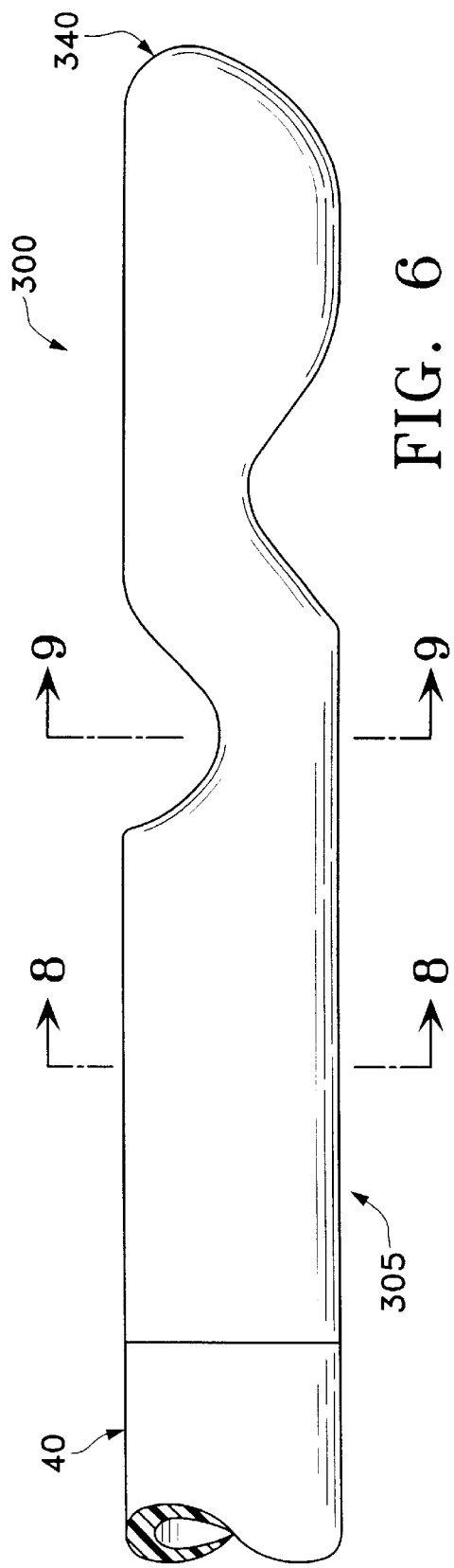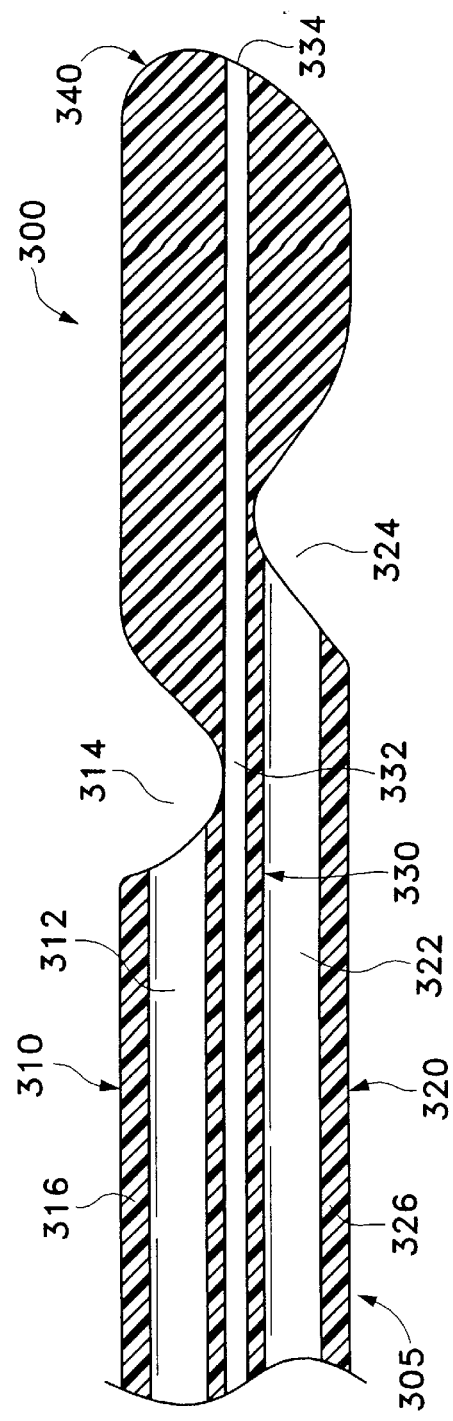

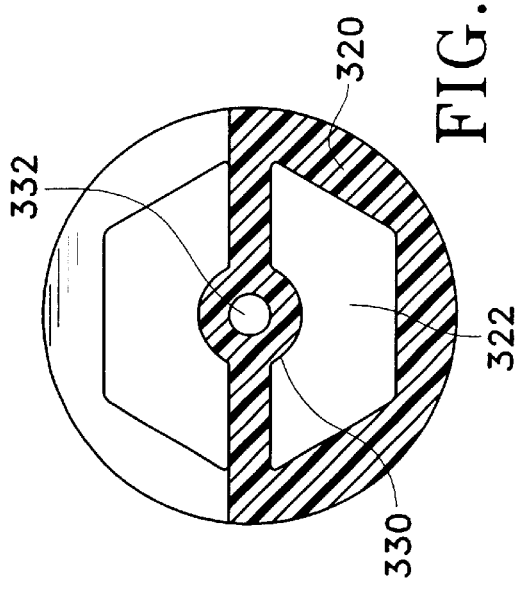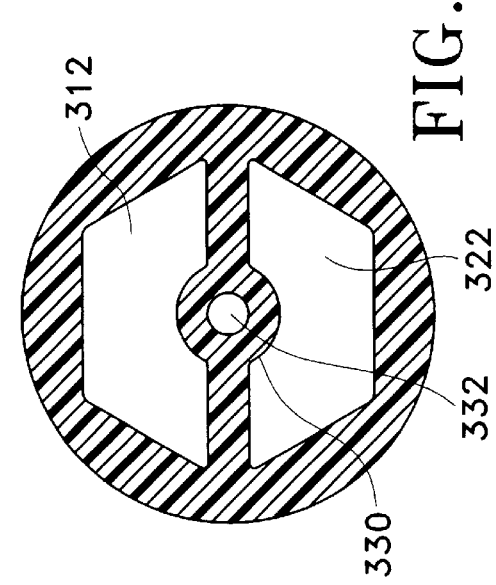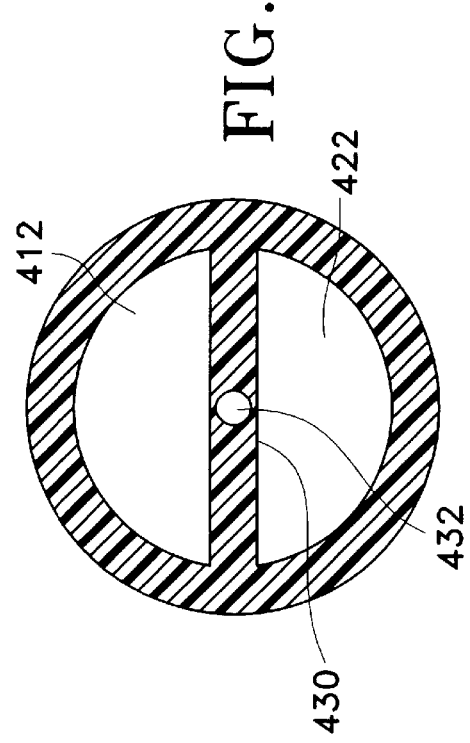

BOLUS TIP DESIGN FOR A MULTI-LUMEN CATHETER

BACKGROUND OF THE INVENTION

1. Field of the Invention

The present invention relates generally to medical devices, and more particularly to an improved tip design for a multi-lumen catheter.

2. Description of Related Art

Multi-lumen catheters are used for a variety of applications when it is necessary to have two separate fluid pathways. One such application for a multi-lumen catheter is for use in a hemodialysis process. During hemodialysis, a dual-lumen catheter can be employed to simultaneously accommodate opposing blood flow. More specifically, one lumen carries blood from a patient to a dialysis machine where it is processed for the removal of toxins, while the opposing lumen returns the purified blood to the patient.

Multi-lumen catheters are well known in the art. An example of such a catheter which is used for hemodialysis is shown in U.S. Pat. No. 4,808,155 to Mahurkar, which discloses a double lumen catheter including a return lumen and an inlet lumen. The return lumen extends along the entire length of the catheter to an opening at the distal end of the catheter. The inlet lumen is shorter than the return lumen and terminates at an opening substantially displaced from the return opening. The separation of the two openings is designed to prevent the mixing of treated blood with non-treated blood. Problems may result from this design, however. First, the openings may become partially or totally occluded by the vessel wall or by a build up of blood components. Second, due to the pressure of fluid exiting the return lumen, a whipping action can occur, wherein the sharp edges of the tip of the catheter lashes back and forth within the vein of a patient, causing trauma to the inside wall of the vein. This whipping action can also cause clots to form around the outside surface of the catheter, obstructing blood flow to and from the openings.

To overcome the problems of the Mahurkar device, Cruz et al. (U.S. Pat. No. 5,571,093) proposed a multi-lumen catheter with a bolus tip, containing a radial passage that forms a port through the side of the bolus. In one embodiment, a first and second lumen are in fluid communication with the port. In another embodiment, the bolus tip contains two ports in the same side, one port providing an opening for the first lumen while the other port provides an opening for the second lumen. In both embodiments, the port nearest to the distal end of the bolus tip is created by removing a piece of the body around greater than 180° of the circumference of the body. According to Cruz et al., this configuration causes the velocity of the fluid passing over the bolus to decrease, thereby limiting the whipping action. However, because the outlets of the first and second lumen are located on the same side of the bolus, the problem of mixing treated and non-treated blood exists. Accordingly, there is a need for a catheter tip configuration that maintains adequate separation of treated and non-treated blood and that reduces the traumatic effects associated with whipping. In addition, there is a need for a catheter tip that will not easily become occluded.

It is therefore an object of this invention to provide an improved bolus tip design for a multi-lumen catheter that provides an optimum separation of fluids to be simultaneously injected into and aspirated from a patient's body.

It is a further object of this invention to provide an improved bolus tip design for a multi-lumen catheter that reduces the trauma to the vein of a patient associated with insertion of the catheter and whipping.

It is still a further object of this invention to provide an improved bolus tip design for a multi-lumen catheter that will allow the continuous transfer of fluid to a patient despite the presence of obstructions.

SUMMARY OF THE INVENTION

The present invention provides an improved bolus tip design for use in a multi-lumen catheter for the simultaneous injection and withdrawal of fluids to and from a patient. The bolus tip includes an elongate body preferably made of either silicone or polyurethane, having two channels for fluid flow. The edges of the bolus tip are rounded to prevent unnecessary trauma to the patient's vein which can occur when the device is initially inserted into the patient, as well as when whipping occurs, which results when fluid being released to the body under pressure causes the device to sway violently back and forth within the vein. An interfacing section at a proximal end of the bolus tip is integrated into the multi-lumen catheter so that the lumens of the catheter match the channels of the bolus tip for uninterrupted flow of fluids therethrough. The integrating of the bolus tip and multi-lumen catheter can be accomplished by one of two procedures. In a first integrating procedure, the bolus tip and catheter are glued together. The outer diameter of the bolus tip at the interfacing point is made slightly greater than that of the multi-lumen catheter so that the catheter can slideably be received by the bolus tip. The bolus tip has a restraining ledge near the bottom of the interfacing section for preventing the further advancement of the catheter during integration. In a second integrating procedure, the bolus tip and catheter are joined through an injection molding process, in which the distal end of a formed catheter is inserted into the bolus tip mold and polyurethane is injected to form the bolus tip with the catheter, resulting in common outer diameters and fluid flow channels.

The two channels, a first channel and a second channel, of the bolus tip run parallel to each other from the catheter to respective outlets, separated by a dividing section. The two channels are generally used for fluid flow, but in certain embodiments, the second channel can be used to house a guide wire for introduction of the catheter into the patient. This is a preferred method of introduction of the catheter over the use of a sheath because of ease, efficiency, and reduced trauma to the patient. The dividing section, in addition to separating the channels, acts as a stabilizing force for the bolus tip by connecting the interfacing section to the nose section. Moreover, in a preferred embodiment, the dividing section also provides a central channel to house the guide wire.

The first channel terminates in a first bolus cavity, which is formed into one side of the bolus tip at a point between the interfacing section and the nose section of the bolus tip. The first bolus cavity extends down to the dividing section in a U-shaped notch, allowing the first channel to be in fluid communication with the surrounding area. The configuration of the first bolus cavity promotes ease of fluid transfer between the bolus tip and the patient, thereby reducing problems associated with the fluid exchange, including whipping and occlusion. Whipping tendency is decreased because the U-shaped configuration effectively slows down the fluid flow. Total occlusion is avoided because even if the surface area of the cavity along the outer diameter of the bolus tip is covered, fluids are still able to enter or exit through the sides of the cavity.

The second channel extends beyond the first channel in the direction of the distal end of the bolus tip. The ending point for the second channel can be configured in one of two ways. In one configuration, the second channel stretches from the interfacing section to the nose section of the catheter. An opening is formed in the end of the catheter which is slightly wider than the second channel itself, facilitating the inlet and outlet of fluids. In another configuration, a second bolus cavity is formed in the side directly opposite the first bolus cavity, located longitudinally between the first bolus cavity and the tip of the nose section. This second bolus cavity also extends to the dividing section in a U-shaped notch, allowing the second channel to be in fluid communication with the surrounding area.

These and other features and advantages of the present invention will become more apparent to those skilled in the art when taken with reference to the following more detailed description of the preferred embodiments of the invention in conjunction with the accompanying drawings.

BRIEF DESCRIPTION OF THE DRAWINGS

FIG. 3 is a longitudinal sectional view of a second embodiment of the present invention.

FIG. 4 is a transverse sectional view taken along line 4—4 of FIG. 1.

FIG. 5 is a transverse sectional view taken along line 5—5 of FIG. 1.

FIG. 6 is a side view of a third embodiment of the present invention.

FIG. 7 is a longitudinal sectional view of FIG. 6.

FIG. 8 is a transverse sectional view taken along line 8—8 of FIG. 6.

FIG. 9 is a transverse sectional view taken along line 9—9 of FIG. 6.

FIG. 10 is transverse sectional view of an alternate configuration for the third embodiment shown in FIG. 7.

DETAILED DESCRIPTION OF THE PREFERRED EMBODIMENTS

Figure 1:
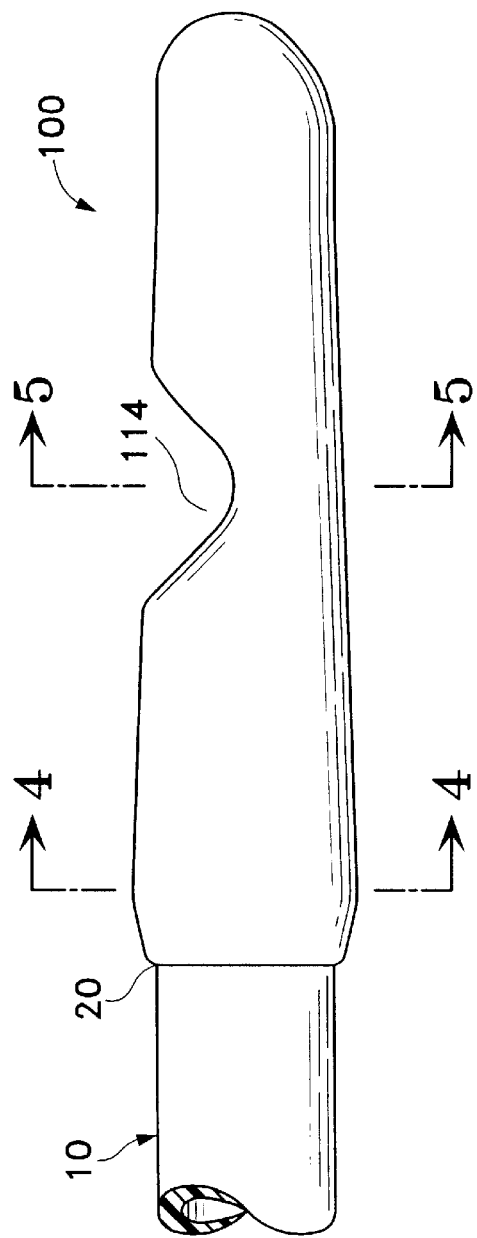
FIG. 1 is a side view of a first embodiment of the present invention.

The present invention satisfies the need for an improved bolus tip design for use with multi-lumen catheters. More particularly, the present invention provides an atraumatic tip design that is efficient and effective in transporting fluids to and from a patient. In the detailed description that follows, it should be appreciated that like reference numerals are used to describe like elements illustrated in one or more of the figures.

Figure 2:
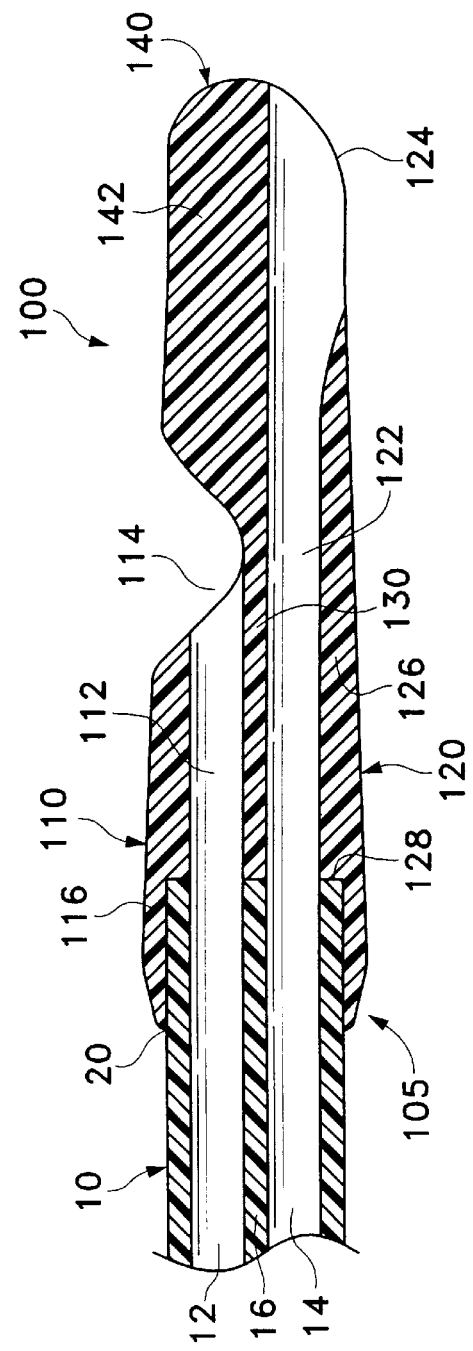
FIG. 2 is a longitudinal sectional view of FIG. 1.

Turning now to FIG. 1, a first embodiment of the present invention is illustrated. A side view of bolus tip 100 is shown coupled to catheter 10 at point 20. A bolus cavity 114 is located in a side of the bolus tip 100 for the entrance or exit of fluids therefrom. FIG. 2 more elaborately illustrates the inventive concepts of the first embodiment. The bolus tip 100 is oblong and rounded, with a U-shaped portion removed from the bolus tip 100, creating the bolus cavity 114. This U-shaped design is beneficial in that it prevents occlusions by providing both top and side access to the channel and limits the tendency of whipping by acting to slow down the passage of fluids. The bolus tip 100 is made of either silicone or polyurethane in the preferred embodiment, but many other materials are possible.

In the sectional view shown in FIG. 2, the bolus tip 100 includes two basic sections, an interfacing section 105 and a nose section 140. The interfacing section 105 further consists of a first section 110, a dividing section 130 and a second section 120. The first section 110 includes a first body section 116, which connects the bolus tip 100 to the catheter 10 and defines the outer wall boundary of a first channel 112 from the edge of the catheter 10 to the bolus cavity 114. The first channel 112 connects to a first lumen 12 of the catheter 10 to form a single contiguous tunnel for uninterrupted flow of fluids therethrough. The first channel 112 terminates at the bolus cavity 114, which provides an access point for the ingress or egress of fluids. The bolus cavity 114 is created by the absence of a significant portion of the first section 110 down to the dividing section 130, forming a U-shape when viewed from the side. The dividing section 130 separates the first channel 112 from the second channel 122, functioning as a stabilizer for bolus tip 100 by preventing internal collapse of the channels and by connecting the interfacing section 105 to the nose section 140. The second section 120 includes a second body section 126 that has a built-in ledge 128 for adeptly receiving catheter 10. The second body section 126 defines an outer wall boundary for a second channel 122 from the edge of catheter 10 to a nose tip opening 124 located in a tip portion 142 of the nose section 140. The tip portion 142 is rounded to lessen the trauma associated with insertion of the catheter and the whipping action of the catheter. The second channel 122 connects with a second lumen 14 of the catheter 10 to provide a smooth transition between the members. The second channel 122 terminates at the nose tip opening 124, which is in fluid communication with the patient. The nose tip opening 124 provides an access point for ingress or egress of fluids into the second channel 122. The second channel 122 can also be used to house a guide wire for introduction of the catheter 10 into the patient. While introduction of the catheter 10 is possible through the use of a sheath, guide wire use is preferred because less trauma to the patient occurs and it is a faster more efficient way to introduce the catheter 10.

The bolus tip 100 and catheter 10 are separately extruded and are affixed to one another through a gluing and/or press fit process at point 20. As seen in FIGS. 1 and 2, the gluing process necessitates a slightly larger diameter for the bolus tip 100 to accommodate the catheter 10 at a point 20 where both the first section 110 and the second section 120 of the bolus tip 100 meet the catheter 10. The first body section 116 incrementally decreases in diameter to match the diameter of the catheter 10 at the bolus cavity 114. Similarly, the diameter of second body section 126 incrementally decreases to match the diameter of the catheter 10. The catheter 10 consists of the first lumen 12, the second lumen 14 and a septum 16. As described above, both passages flow continuously into their counterparts in bolus tip 100 to form an uninterrupted channel for fluid flow to and from the patient.

Turning to FIG. 3, a second embodiment of the bolus tip design is shown. A bolus tip 200 is coupled to the catheter 10 at a point 30, in the same way as explained above with reference to FIG. 2. The catheter 10 is fastened to bolus tip 200, the two being pressed together until the point that the catheter 10 is stopped by a ledge 228. As in the first embodiment, the diameter of the bolus tip 200 is slightly larger than the catheter 10 at the joining point 30, but gradually decreases over the length of the bolus tip 200 so that a nose section 240 is the same diameter as the catheter 10. The bolus tip 200 includes an interfacing section 205 and the nose section 240. The interfacing section 205 further consists of a first section 210, a dividing section 230 and a second section 220. The first section 210 and the dividing section 230 are similar in form and function to the first embodiment, defining a first channel 212 which terminates at a first bolus cavity 214. As in the first embodiment, the first bolus cavity 214 is an access point for the ingress and egress of fluids to and from the catheter 10. The second section 220 differs from the first embodiment in that a second interfacing section 226, together with the dividing section 230 define a second channel 222 which opens into a second bolus cavity 224, located longitudinally between first bolus cavity 214 and a tip portion 242 of the nose section 240.

As in the first embodiment, the tip portion 242 is rounded for preventing unnecessary trauma to the vein of the patient. The second bolus cavity 224 is created in the same manner as the first bolus cavity 214, namely by removing a U-shaped portion from the bolus tip 200.

FIG. 4 is a cross-sectional view of the bolus tip 100 taken along line 4—4 in FIG. 1. The interfacing section 105 is seen encompassing the catheter 10. The first lumen 12 and the second lumen 14 of the catheter 10 are shown separated by the septum 16, both lumens being D-shaped in the preferred embodiment. It is possible, however, for these lumens, as well as their accompanying channels of the bolus tip 100, to take on a variety of different shapes. FIG. 5 is a cross-sectional view of the bolus tip 100 taken along line 5—5 in FIG. 1, through the bolus cavity 114. This view illustrates the D-shape of the second channel 122 defined by the second section 120 and the dividing section 130.

Turning now to FIG. 6, a third embodiment of the present invention is shown of a bolus tip 300 attached to a catheter 40. This embodiment differs from the previous two embodiments in two aspects. First, the bolus tip 300 has a central channel 332 extending through a dividing section 330 for the passage of a guide wire, as shown in FIG. 7; a septum (not shown) of catheter 40 has a central lumen (not shown) that is directly linked to the central channel 332. Second, the connection between the bolus tip 300 and the catheter 40 is different in that, instead of gluing the catheter 10 into the bolus tip 300, the two are completely joined through an injection molding process, wherein the distal end of the already formed catheter 40 is placed into the mold for the bolus tip 300 prior to injection. This results in common outer diameters and fluid flow channels for catheter 40 and bolus tip 300. FIG. 7 illustrates the bolus tip 300 by showing a longitudinal cross-sectional view of the third embodiment. Like the first two embodiments, the bolus tip 300 includes an interfacing section 305 and a nose section 340. The interfacing section 305 further consists of a first section 310, a second section 320 and a dividing section 330. Similar to the second embodiment shown in FIG. 3, a first body section 316 and a second body section 326 define the first and second portions of channels 312 and 322 respectively. The first channel 312 terminates in a first bolus cavity 314, while the second channel 322 terminates in a second bolus cavity 324 in a configuration similar to that of the second embodiment. The dividing section 330 includes the central channel 332 running throughout the length of the bolus tip 300, through the rounded nose section 340. The central channel 332 is sized to accommodate a guide wire for easy insertion of catheter 40 and bolus tip 300 into a targeted area of the patient's body.

FIGS. 8 and 9 show cross-sectional views along lines 8—8 and 9—9 in FIG. 6 respectively. The first channel 312 and the second channel 322 are shown with trapezoidal-like shapes, the bases of each trapezoidal channel being partially carved out by the intersection of the dividing section 330. FIG. 10 shows an alternate embodiment for a cross section along the line 8—8, wherein channels 412 and 422 are D-shaped, with no alteration to the shape of the channels coming from the dividing section 430.

Many alterations and modifications may be made by those having ordinary skill in the art without departing from the spirit and scope of the present invention. For example, the second bolus cavity is disclosed as being located directly opposite the first bolus cavity. It should be apparent, however, that the inventive concepts described above would be equally applicable to a configuration where the second bolus cavity is located on a side adjacent to the first bolus cavity. Moreover, the words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

What is claimed is:

1. A multi-lumen catheter apparatus for use in the simultaneous injection of fluids to, and aspiration of fluids from, a targeted area of a patient, comprising a catheter body and a bolus tip, wherein said catheter body comprises an outer wall and a septum that together form a first and second lumen, and wherein said bolus tip is separate from and connected to a distal end of said catheter body, said bolus tip comprising:

an elongate body, having a substantially cylindrical shape defined by an outer wall;

an interfacing section at a proximal end of said elongate body, comprising a dividing section that divides said elongate body into a first channel and a second channel, wherein said first lumen is in fluid communication with said first channel and said second lumen is in fluid communication with said second channel;

a nose section at a distal end of said elongate body, comprising a tip having a semispheroidal shape;

a first cavity formed in a first side of said elongate body in fluid communication with said first channel; and a second cavity formed in a second side of said elongate body in fluid communication with said second channel;

wherein a mid-portion of said first and second cavities extends through the entirety of said elongate body outer wall to said dividing section on respective said first and second sides of said elongate body.

2. The multi-lumen catheter apparatus of claim 1, wherein the longitudinal length of said second channel is greater than the longitudinal length of said first channel.

3. The multi-lumen catheter apparatus of claim 1, wherein said second cavity is longitudinally located between said first cavity and said tip of said nose section.

4. The multi-lumen catheter apparatus of claim 1, wherein said septum defines a third lumen and said dividing section defines a third channel, wherein said third lumen is in fluid communication with said third channel, and wherein said third channel extends through said tip of said nose section.

5. The multi-lumen catheter apparatus of claim 1, wherein the cross-section of said first channel and said second channel is D-shaped.

6. The multi-lumen catheter apparatus of claim 1, wherein a cross-section of said first channel and said second channel is trapezoidal-shaped.

7. A bolus tip configured for connection to a distal end of a catheter body, being initially separate therefrom, comprising:

an elongate body, having a substantially cylindrical shape defined by an outer wall;

an interfacing section at a proximal end of said elongate body, comprising a first channel, a dividing section, and a second channel, wherein said dividing section separates said first channel from said second channel;

a nose section at a distal end of said elongate body, comprising a tip having a semispheroidal shape;

a first cavity formed in a first side of said elongate body in fluid communication with said first channel; and a second cavity formed in a second side of said elongate body in fluid communication with said second channel;

wherein a mid-portion of said first and second cavities extends through the entirety of said outer wall to said dividing section on respective said first and second sides of said elongate body.

8. The bolus tip of claim 7, wherein the longitudinal length of said second channel is greater than the longitudinal length of said first channel.

9. The bolus tip of claim 7, wherein said second cavity is longitudinally located between said first cavity and said tip of said nose section.

10. The bolus tip of claim 7, wherein said dividing section defines a third channel that extends through said tip of said nose section.

11. The bolus tip of claim 7, wherein the cross-section of said first channel and said second channel is D-shaped.

12. The bolus tip of claim 7, wherein a cross-section of said first channel and said second channel is trapezoidal-shaped.

13. A dual-lumen catheter, comprising a catheter body having separate first and second lumens, and a catheter tip comprising a first opening in fluid communication with said first lumen and a second opening in fluid communication with said second lumen, said first opening being formed in a first side of said catheter tip and comprising a portion extending through the entirety of an outer wall on said first side of said catheter tip to a dividing section, said second opening being formed in a second side of said catheter tip and being positioned distal of said first opening.

14. The dual-lumen catheter according to claim 13, wherein said second opening is formed in a nose section of said catheter tip.

15. The dual-lumen catheter according to claim 13, wherein said dividing section comprises a channel.

* * * * *